(12) United States Patent
Koc et al.

(10) Patent No.: US 12,611,541 B2
(45) Date of Patent: Apr. 28, 2026

(54) POWERING SYSTEM FOR CONSTANT CURRENT NEURAL STIMULATORS

(71) Applicant: ORTA DOGU TEKNIK UNIVERSITESI, Ankara (TR)

(72) Inventors: Mert Koc, Ankara (TR); Salar Chamanian, Ankara (TR); Haluk Kulah, Ankara (TR)

(73) Assignee: ORTA DOGU TEKNIK UNIVERSITESI, Ankara (TR)

( * ) Notice: Subject to any disclaimer, the term of this patent is extended or adjusted under 35 U.S.C. 154(b) by 411 days.

(21) Appl. No.: 18/261,286

(22) PCT Filed: Jan. 13, 2021

(86) PCT No.: PCT/TR2021/050019
§ 371 (c)(1),
(2) Date: Jul. 13, 2023

(87) PCT Pub. No.: WO2022/154758
PCT Pub. Date: Jul. 21, 2022

(65) Prior Publication Data
US 2024/0066301 A1     Feb. 29, 2024

(51) Int. Cl.
| | |
|---|---|
| *A61N 1/36* | (2006.01) |
| *A61N 1/378* | (2006.01) |
| *H02J 7/00* | (2026.01) |
| *H02J 50/00* | (2016.01) |
| *H02M 3/155* | (2006.01) |

(52) U.S. Cl.
CPC ..... *A61N 1/36125* (2013.01); *A61N 1/36146* (2013.01); *A61N 1/3787* (2013.01); *H02M 3/155* (2013.01)

(58) Field of Classification Search
CPC ............ A61N 1/36125; A61N 1/36146; A61N 1/3787; A61N 1/3785; A61N 1/3605; H02J 7/0063; H02J 50/00; H02J 50/001; H02J 2207/20; H02J 2310/23
See application file for complete search history.

(56) References Cited

U.S. PATENT DOCUMENTS

| | | | |
|---|---|---|---|
| 7,519,428 | B1 | 4/2009 | Palmer |
| 9,079,032 | B2 | 7/2015 | Ternes et al. |
| 9,731,116 | B2 | 8/2017 | Chen |
| 12,390,644 | B1 * | 8/2025 | Mathur .............. A61N 1/36125 |

(Continued)

FOREIGN PATENT DOCUMENTS

WO      2006029007 A2     3/2006

OTHER PUBLICATIONS

Hasan Ulusan, et al., A Sub-500 μW Interface Electronics for Bionic Ears, IEEE Access, 2019, pp. 132140-132152, vol. 7.

(Continued)

*Primary Examiner* — Sisay G Tiku
(74) *Attorney, Agent, or Firm* — Bayramoglu Law Offices LLC

(57) ABSTRACT

A powering system for constant current neural stimulators provides adaptive supply voltage for neural stimulators to decrease power dissipation by taking advantage of varying voltage compliance of constant current stimulation. The powering system includes an adaptive voltage supply generator, a monitoring circuit, a charge pump, a step-down converter, and a rechargeable battery.

11 Claims, 15 Drawing Sheets

(56) References Cited

U.S. PATENT DOCUMENTS

| | | | |
|---|---|---|---|
| 2007/0097719 A1* | 5/2007 | Parramon | H02M 3/155 |
| | | | 363/72 |
| 2010/0211132 A1* | 8/2010 | Nimmagadda | H02M 3/156 |
| | | | 607/60 |
| 2012/0277830 A1* | 11/2012 | Arfin | A61N 1/36125 |
| | | | 607/62 |
| 2013/0066400 A1 | 3/2013 | Perryman et al. | |
| 2013/0314129 A1 | 11/2013 | Yao et al. | |
| 2014/0243926 A1 | 8/2014 | Carcieri | |
| 2018/0071512 A1* | 3/2018 | Feldman | A61N 1/05 |
| 2021/0008373 A1* | 1/2021 | Single | A61N 1/0551 |
| 2022/0023638 A1* | 1/2022 | DeShazo | A61N 1/36125 |
| 2023/0107780 A1* | 4/2023 | Weerakoon | G05F 3/26 |
| | | | 323/234 |

OTHER PUBLICATIONS

Wannaya Ngamkham, et al., Biphasic Stimulator Circuit for a Wide Range of Electrode-Tissue Impedance Dedicated to Cochlear Implants, 2012, pp. 1083-1086.

B. Swanson, et al., Impedance measurement of the Nucleus 22-electrode array in patients, Annals of Otology, Rhinology & Laryngology, 1995, pp. 141-144, vol. 104.

Ji-Jon Sit, et al., A Low-Power Blocking-Capacitor-Free Charge-Balanced Electrode-Stimulator Chip With Less Than 6 nA DC Error for 1-mA Full-Scale Stimulation, IEEE Transactions on Biomedical Circuits and Systems, 2007, pp. 172-183, vol. 1 No. 3.

Marek S. Makowski, et al., Performance Limits of Switched-Capacitor DC-DC Converters, IEEE, 1995, pp. 1215-1221.

Younis Allasasmeh, et al., High-Performance Switched-Capacitor Boost-Buck Integrated Power Converters, IEEE Transactions on Circuits and Systems-I: Regular Papers, 2018, pp. 3970-3983, vol. 65 No. 11.

* cited by examiner

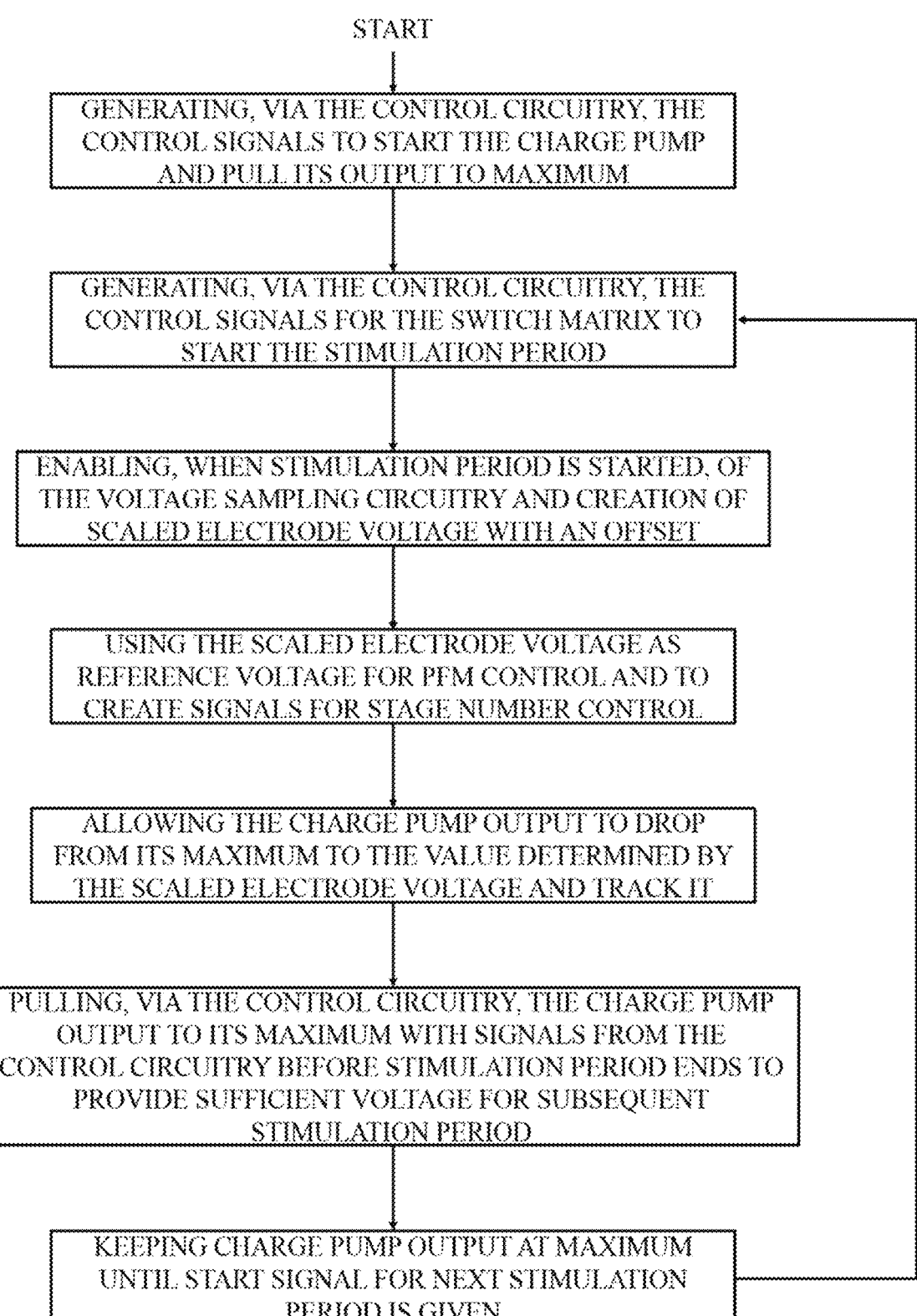

START

GENERATING, VIA THE CONTROL CIRCUITRY, THE CONTROL SIGNALS TO START THE CHARGE PUMP AND PULL ITS OUTPUT TO MAXIMUM

GENERATING, VIA THE CONTROL CIRCUITRY, THE CONTROL SIGNALS FOR THE SWITCH MATRIX TO START THE STIMULATION PERIOD

ENABLING, WHEN STIMULATION PERIOD IS STARTED, OF THE VOLTAGE SAMPLING CIRCUITRY AND CREATION OF SCALED ELECTRODE VOLTAGE WITH AN OFFSET

USING THE SCALED ELECTRODE VOLTAGE AS REFERENCE VOLTAGE FOR PFM CONTROL AND TO CREATE SIGNALS FOR STAGE NUMBER CONTROL

ALLOWING THE CHARGE PUMP OUTPUT TO DROP FROM ITS MAXIMUM TO THE VALUE DETERMINED BY THE SCALED ELECTRODE VOLTAGE AND TRACK IT

PULLING, VIA THE CONTROL CIRCUITRY, THE CHARGE PUMP OUTPUT TO ITS MAXIMUM WITH SIGNALS FROM THE CONTROL CIRCUITRY BEFORE STIMULATION PERIOD ENDS TO PROVIDE SUFFICIENT VOLTAGE FOR SUBSEQUENT STIMULATION PERIOD

KEEPING CHARGE PUMP OUTPUT AT MAXIMUM UNTIL START SIGNAL FOR NEXT STIMULATION PERIOD IS GIVEN

FIG. 15

POWERING SYSTEM FOR CONSTANT CURRENT NEURAL STIMULATORS

CROSS REFERENCE TO THE RELATED APPLICATIONS

This application is the national phase entry of International Application No. PCT/TR2021/050019, filed on Jan. 13, 2021, the entire contents of which are incorporated herein by reference.

TECHNICAL FIELD

The invention relates to which is related to a powering system for constant current neural stimulators that provides adaptive supply voltage for neural stimulators to decrease power dissipation by taking advantage of varying voltage compliance of constant current stimulation.

BACKGROUND

Neural stimulation has been utilized for the treatment or improvement of those who have impairments in specific limbs or organs. Cochlear implants can be given as an example to devices that utilize neural stimulation, as they mimic the operation of the cochlea to enable hearing for people with sensorineural hearing loss. Additionally, pacemakers, retinal implants, or neural stimulation for pain relief can be given to applications where neural stimulation devices are utilized.

To perform neural stimulation, several methods can be adopted, namely, voltage mode, charge mode and current mode. Voltage mode is the most efficient mode, however, does not provide control on the total charge provided. With charge mode, this is controllable, however, this mode requires large capacitors for sufficient charge delivery. Current mode, despite its lower efficiency is the most popular thanks to its safety and wide load range US20130314129A1.

In the literature, biphasic current pulses, as shown in FIG. 1B, are used for constant current stimulation. A two-phase current is utilized to decrease the power dissipation and conserve the charge balance of the neuron. Stimulation is performed with electrodes and the electrode voltage difference corresponding to current stimulation is also shown in FIG. 1B. The reason for this voltage waveform is the electrode tissue interface, or the load impedance, which can be modelled as shown in FIG. 1A. Bulk resistor (Rbulk) models the substance between two electrodes, whereas the electrode-tissue interface is modelled with a capacitor (Csurf). The leakage resistor (Rleak) is used to model the redox reactions occurring at the electrode surface that is connected in parallel with the Csurf [7]. Moreover, Rleak is typically ignored due to its greater value [5], [6], [7], [8].

Creation of a biphasic pulse can be done by different implementations. Examples to various implementations are given below, where multiple current sources are used, as shown in FIG. 2A U.S. Pat. No. 7,519,428B1, a recharge capacitor (955) is utilized, as provided in FIG. 2B U.S. Pat. No. 9,079,032B2, or a simple switch configuration is made used of, similar to the one in FIG. 3.

As mentioned before, neural stimulators perform their tasks on either organs or limbs and in most cases, in volume constrained scenarios. This brings the issue of low capacity battery with it. Moreover, in most cases these batteries are surgically placed inside the human body, so, when their performances have degraded critically due to many charging cycles or in the case when they are not rechargeable, they need to be replaced. To reduce the discomfort and issues concerning the replacement operation, these implant devices must be made to be as efficient as possible, which has led to studies working on this issue.

A specific aspect of the neural stimulator that has been focused on is the voltage compliance issue. For the load impedance given in FIG. 1A, the created voltage across the electrodes can be calculated for specific stimulation current with equation (1) and thus, the necessary voltage compliance can be determined. To illustrate, for 9 kΩ and 20 nF load impedance the calculated voltage for 1 mA and 50 us stimulation current and duration is 11.5 V. However, this value drops to 5.75 V for a stimulation current of 500 μA. If both scenarios were to be supplied with 12 V, power would be wasted in the second condition. This aspect of neural stimulation is taken advantage of to reduce the power dissipation. In the next section, several studies are summarized which work on this issue.

$$V_{comp} = I_{stim}R_{bulk} + \frac{1}{C_{surf}}I_{stim}\Delta t \tag{1}$$

Contrary to some implementations, rather than modifying the supply voltage, the work presented in US20130314129A1 modifies the stimulation current itself. If the high voltage monitoring block in the stimulator detects that the output voltage on the electrode is smaller than a predefined threshold voltage, the stimulation current for the subsequent stimulation is modified. The modification can be done to the waveform shape, pulse width, amplitude etc. One specific example is decreasing the pulse width and increasing the amplitude of the stimulation current. This way, the head room between the electrode voltage and supply voltage is decreased and less power is wasted.

As mentioned before, multiple current sources are utilized in U.S. Pat. No. 7,519,428B1. In case of high voltage compliance, the electrodes are connected to a current source and sink with positive and negative supply, respectively. This is done interchangeably, to create a biphasic pulse. When low voltage compliance is needed, one of the electrodes is always connected to ground and the other electrode is connected to a current source in one phase and a current sink in the other phase.

In U.S. Pat. No. 9,079,032B2, an electrostimulation energy storage capacitor's voltage is monitored, and the load impedance is calculated for a specific stimulation current by observing how the storage capacitor is discharged. Additionally, a recharge capacitor is connected between the load and ground so that the opposite phase of the stimulation current can be generated.

The design in U.S. Pat. No. 9,731,116B2 also uses the output capacitor of a charge pump where it is charged to a specific voltage before the stimulation for a certain amount of time determined by the controller. For high stimulation currents where the output capacitor is discharged too much, the charge pump is re-enabled to charge the output capacitor once again so that voltage compliance is maintained, and correct stimulation can be performed.

The designs above either use the information of previous stimulation currents or need complicated circuitry. Additionally, they only operate at discreet voltage values. The device presented here monitors the electrode voltages resulting from constant current stimulation and adapts itself so that it follows the electrode voltage difference with a certain amount of headroom in order to provide enough voltage compliance. An example ideal waveform which is trying to be achieved can be seen in FIG. 4. Towards the end of a stimulation period, the supply voltage is pulled up to a predefined high voltage value to prepare for the subsequent stimulation period. In addition, in this interval necessary charge balancing methods can be utilized to prevent the neurons from getting damaged due to potential build up. In the subsequent sections the overall system and the adaptive voltage supplier are explained.

SUMMARY

The present invention is related to a powering system for constant current neural stimulators that meets the requirements mentioned above, eliminates all of the disadvantages and brings about some new advantages.

This invention describes a powering system that provides adaptive supply voltage for neural stimulators to decrease power dissipation by taking advantage of varying voltage compliance of constant current stimulation. Stimulation electrodes' voltages are monitored to determine the necessary supply voltage. Subsequently, frequency of operation and the number of operational charge pump stages are adjusted accordingly to provide voltage compliance for the stimulation circuitry. Additionally, a step-down converter is used to power the control circuitry to further bring down the power loss. An energy harvester and appropriate interface circuitry is utilized to charge the battery for uninterrupted operation for prolonged period of time.

BRIEF DESCRIPTION OF THE DRAWINGS

The figures used to better explain a developed with a powering system for constant current neural stimulators this invention and their descriptions are as follows.

4

Figure 14:
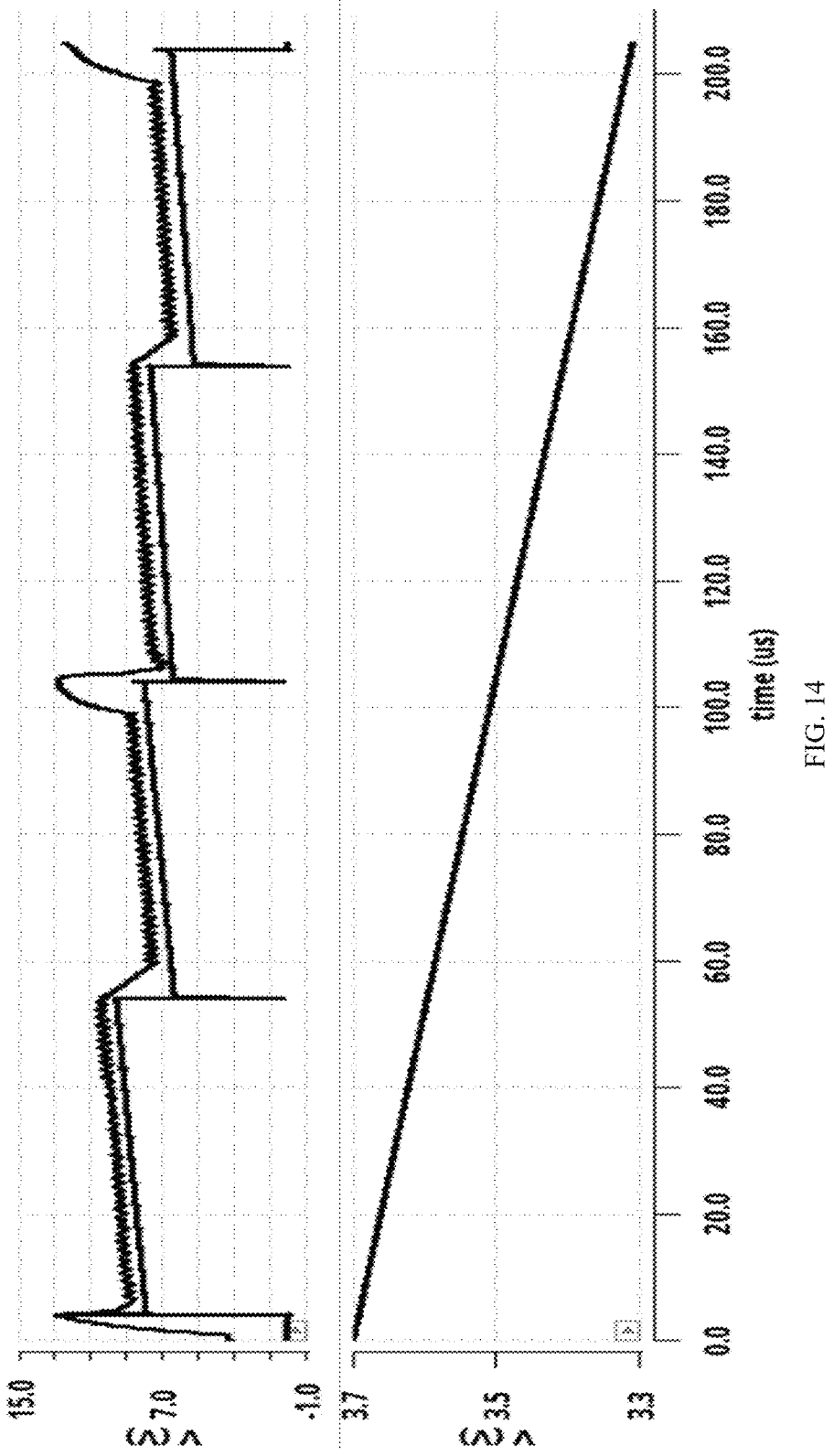

FIG. 14: Example waveform for charge pump output and absolute value of electrode voltages for varying load when battery voltage (bottom) is varied from 3.7 V to 3.3 V in 200 μs.

FIG. 15: Operation method of the invention.

DETAILED DESCRIPTION OF THE EMBODIMENTS

To better explain developed a powering system for constant current neural stimulators with this invention, the details are as presented below.

Figure 5:
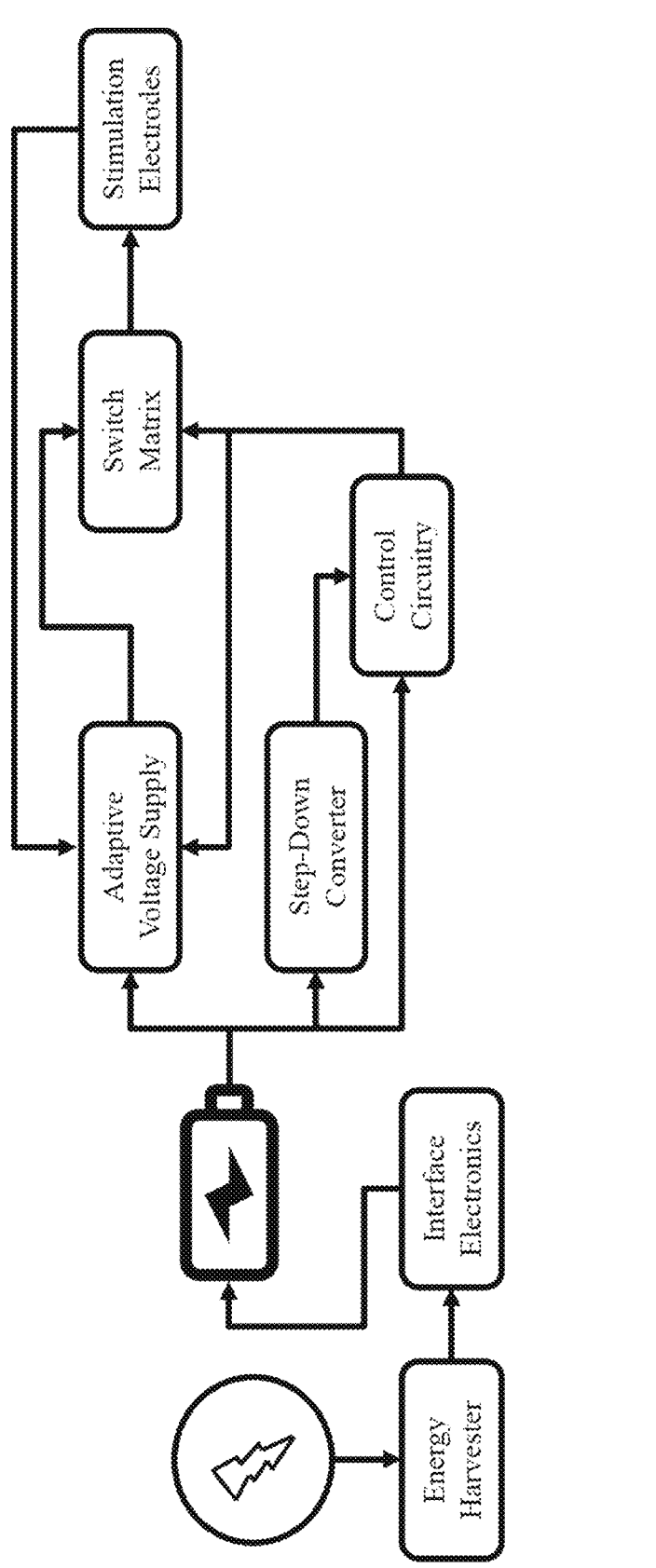
FIG. 5: Block diagram of the overall neural stimulation system.

The block diagram of the overall system can be seen in FIG. 5. The adaptive voltage supply and the step-down converter are operated from a battery cell. In some examples, the battery can be rechargeable or non-rechargeable. In the rechargeable case, besides being able to charge the battery from an external source, such as a wireless power transmitter, the battery can be charged by using an energy harvester with the utilization of the proper interface circuitry. This will prolong the period of time the devices can be operated before having to charge it. In some examples, the energy harvester might not be included in the system and the battery will be charged from an external source or the battery might not be rechargeable at all.

Besides the adaptive voltage supply generator, a step-down converter is utilized to decrease the power dissipation of the control circuitry. In some examples, this step-down converter can be comprised of a switched-capacitor converter to obtain a fully integrated design. In some examples, it can be a resonant or multi-level switching converter, which includes both capacitive and inductive elements. In some cases, for the step-down converter, a linear converter can be utilized to decrease size and complexity.

Figure 1B:
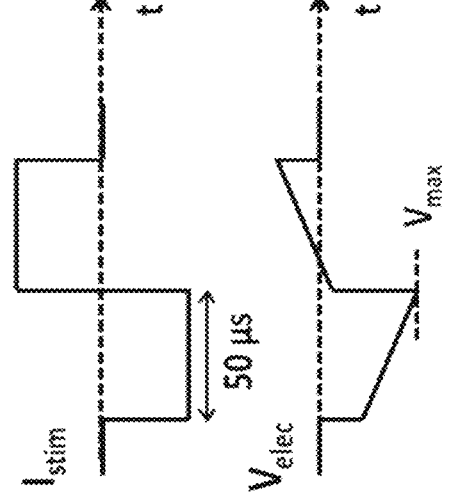
FIGS. 1A and 1B: Biphasic current pulse used to stimulate the neurons (Previous technic).
Figure 1A:
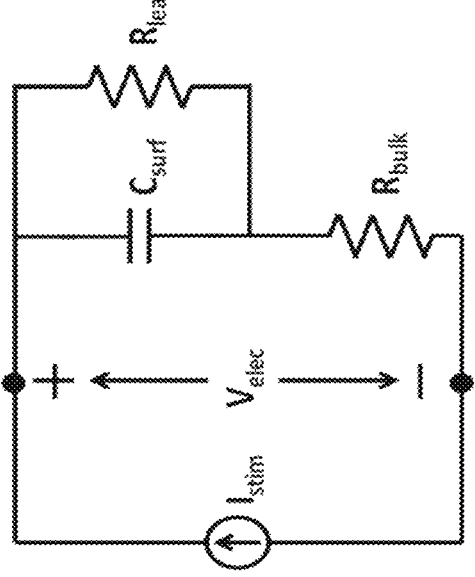
Figures 2A, 2B:
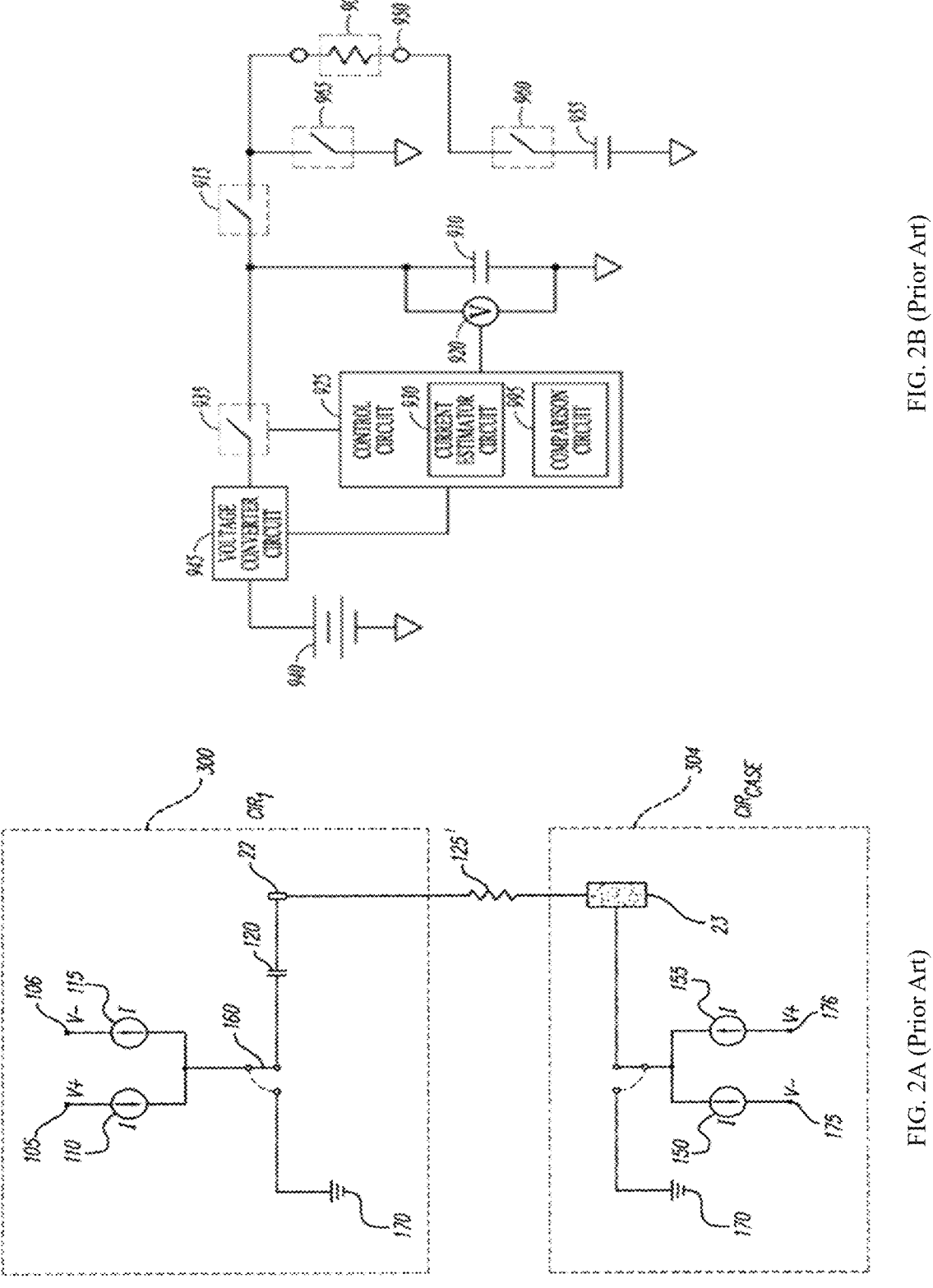
FIGS. 2A and 2B: Example implementations to biphasic pulse generation (a) by using multiple current sources U.S. Pat. No. 7,519,428B1 and (b) by utilizing a recharge capacitor (Previous technic).
Figure 3:
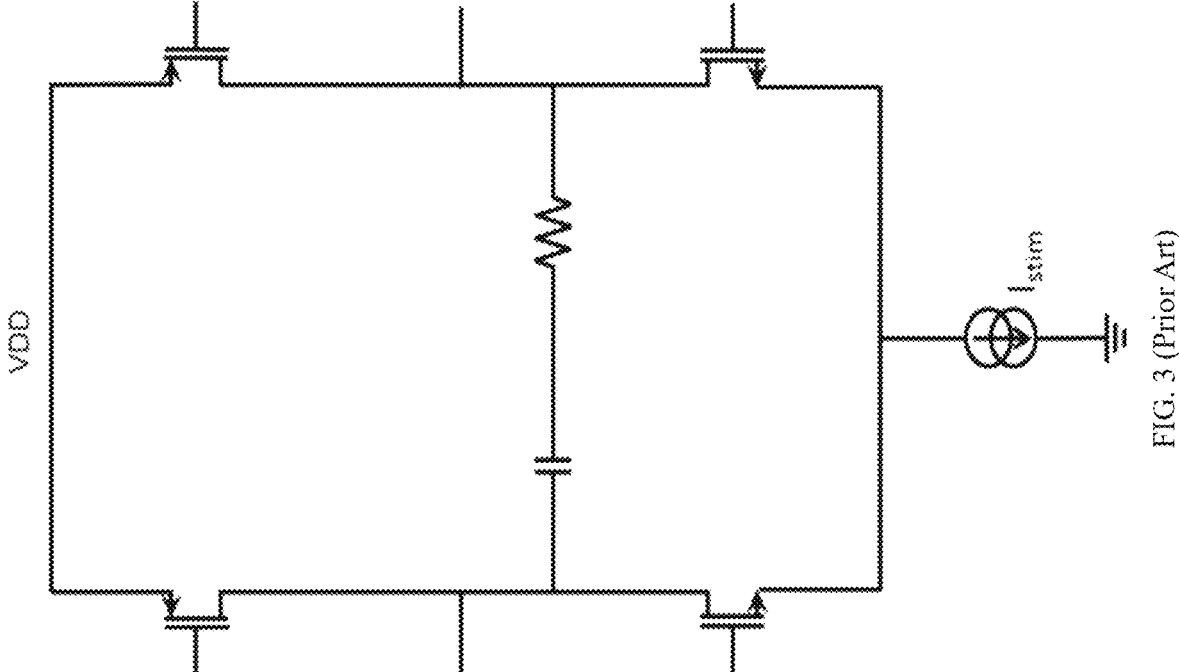
FIG. 3: An example switch configuration for biphasic pulse generation (Previous technic).
Figure 4:
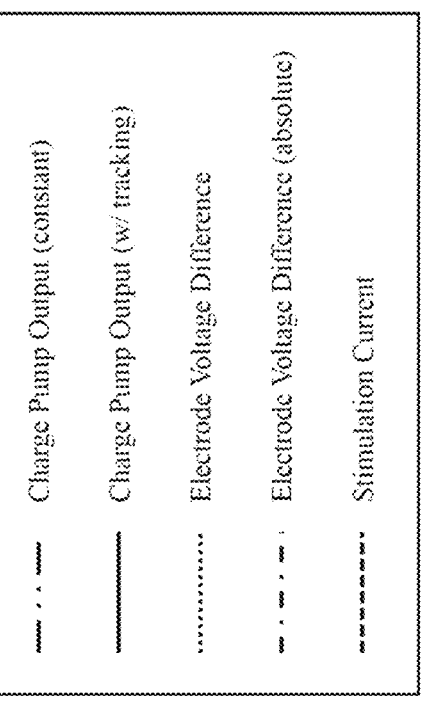
FIG. 4: Example of constant supply voltage and electrode voltage tracking supply voltage
Figure 4:
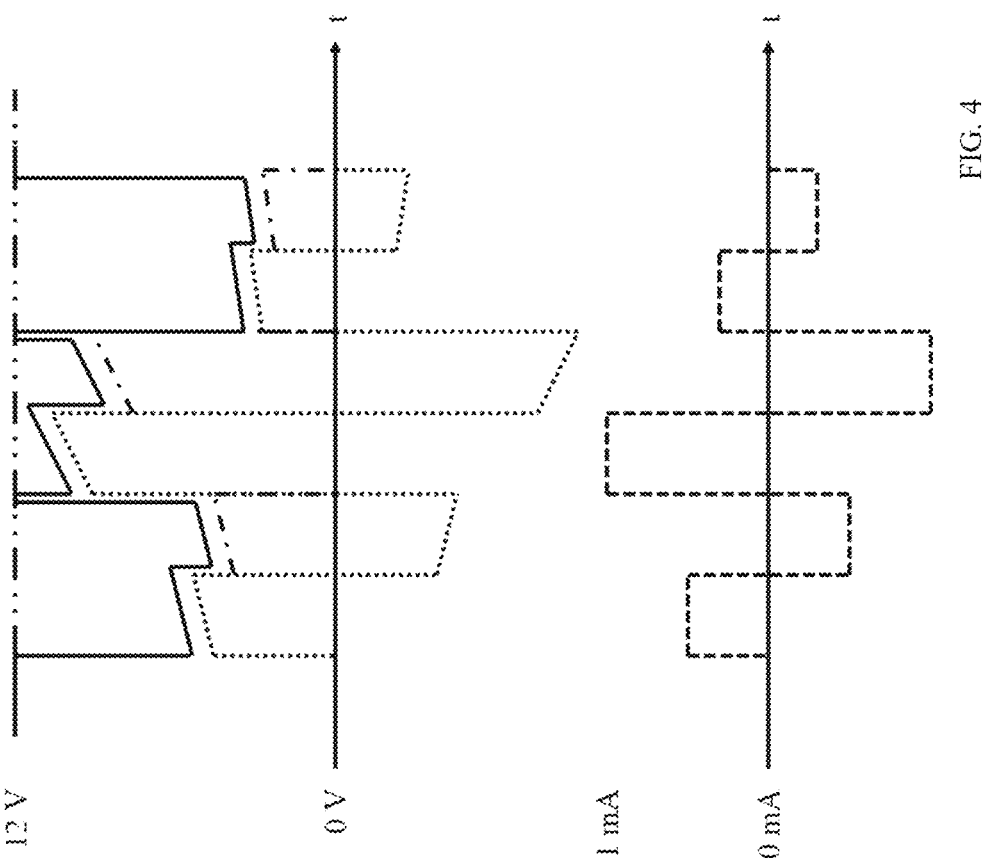

Moreover, as mentioned, an adaptive voltage supply is used in this system. The main task of the adaptive voltage supply is to provide the switch matrix, which is used to create the necessary stimulation signal for the stimulation electrodes, with right amount of voltage to ensure voltage compliance. To do this, it monitors the voltage on the stimulation electrodes and creates a supply voltage which tracks that voltage with a certain amount of voltage headroom, as was shown in FIG. 4. The next section will explain the adaptive voltage supply generator further.

Adaptive Voltage Supply

Figure 6:
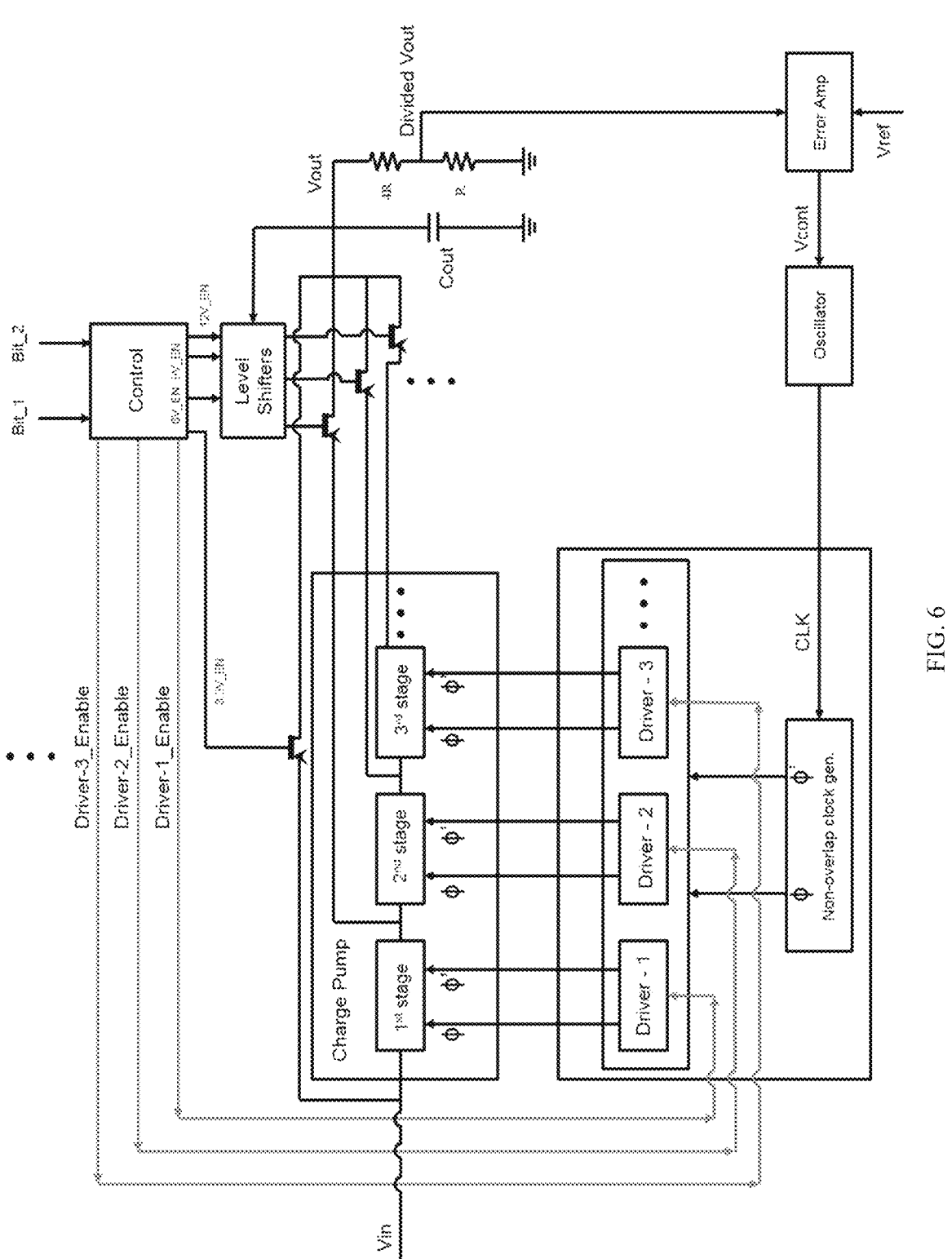
FIG. 6: Block diagram of the charge pump side of the design.

Overall description of the Adaptive Voltage Supply Generator:

The overall design is represented with two block diagrams. The first one, shown in FIG. 6, is the charge pump side of the design. As mentioned, the charge pump voltage tracks the electrode voltage. The tracking is performed in two ways. First one is the control of number of charge pump stages utilized and second is frequency control.

Controlling the number of stages enables rough control of the output voltage. For instance, for an input voltage of 3.3 V and output voltages from 3 to 6 V, only one stage is operational while for 9 to 12 V all three stages must be utilized. This is adopted due to the inherent decrease in charge pump efficiency when the output voltage is deviated from the discrete value the charge pump is providing [9]. For an input voltage of 3.3 V, the 3-stage charge pump, which quadruples the input voltage would be most efficient when supplying voltages close to 13.2 V. Thus, to prevent dramatic efficiency loss at lower voltage the voltage range is divided into three parts in which different levels of voltages can be provided. This is summarized in Table 1. In this table, Bit_1 and Bit_2 are control signals which determine the number of stages operational. These control signals are provided from the second part of the design, which will be explained next.

This version of the adaptive voltage supply generator utilizes a three-stage charge pump, however, according to the necessary voltage to be supplied to the neural stimulator, the number of stages can be increased. Accordingly, control circuitry, drivers, level shifters and the second part of the design, which will be explained, must be modified as well. In another example, other topologies of charge pumps can be utilized. Similar to this configuration, the topology of the design in those examples might need to be configured as well. In other examples, utilizing pulse width modulation (PWM) or pulse frequency modulation (PFM) control, as explained next, might be enough.

Moreover, fine control of the output voltage is achieved by controlling the output impedance of the charge pump, which is achieved by frequency control. For this, an error amplifier and a voltage controlled oscillator (VCO) is utilized. The error amplifier creates a control voltage for the VCO by comparing the divided charge pump output voltage and a reference voltage, which, again, is supplied by the second part of the design. In some examples, ripple control method can be used to enable and disable the clock signal fed to the non-overlapping clock generator so that a regulated voltage can be achieved.

TABLE 1

Output voltage intervals corresponding to control bits and # of charge pump stages operational.

| Bit_2 | Bit_1 | $V_{out}$ | # of stage operating |
|-------|-------|-----------|----------------------|
| 0 | 0 | 3.3 | 0 |
| 0 | 1 | 3.3-6 V | 1 |
| 1 | 0 | 6-9 V | 2 |
| 1 | 1 | 9-12 V | 3 |

Figure 7:
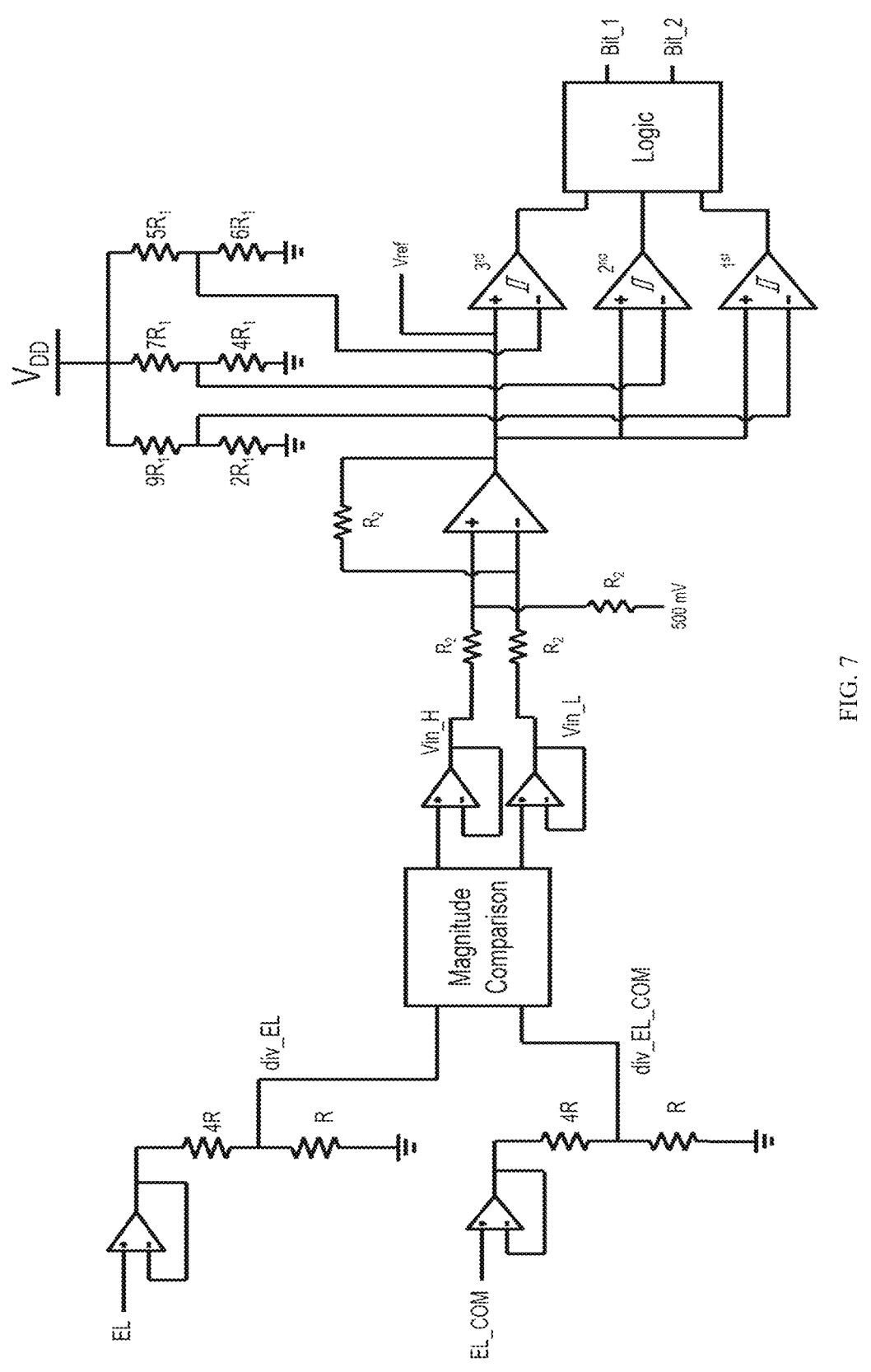
FIG. 7: Block diagram for the second part of the design.

The block diagram for the second part of the design, which is voltage sampling and control signal generation, is provided in FIG. 7. EL is the channel electrode and EL_COM is the common electrode. In the first part the electrode voltages are sampled and fed through to the subtraction circuitry. In the subtraction part, their magnitudes are compared to determine which electrode has greater potential as it changes depending on the phase of the biphasic pulse. This is to ensure that the difference amplifier used to perform the subtraction is operating properly. In other examples, the magnitude comparison might not be necessary if a circuit is used which can perform correct subtraction independent on which electrode voltage is subtracted from which.

Consequently, the electrode voltages are subtracted and given a certain amount of offset and fed to a flash ADC, which is then mapped to two bits. These are Bit_1 and Bit_2, which were also shown in FIG. 6. The comparing voltages for the hysteresis comparators are created with a resistive division so that the correct number of charge pump stages are operational for the desired voltage compliance. The hysteresis comparators determine whether a charge pump stage is operational or not. To illustrate, for an input voltage of 3.3 V, a two-stage charge pump would be able to provide 9.9 V output voltage under no load condition. Thus, keeping the load conditions in mind, the design should operate such that the third stage is not operational until the necessary output voltage does not reach 9 V. Beyond this value, the third stage should be operational as well. Assuming that the voltage divider in FIG. 6 provides ⅕th of the charge pump output voltage, a reference voltage of 1.8 V would be needed for the error amplifier and oscillator to keep the output voltage at 9 V. As mentioned, if the results of the subtraction in FIG. 7 exceeds 1.8 V, the third stage should start operating, which is when the third hysteresis comparator changes its output to HIGH and the third stage starts operating. As can be seen in FIG. 7, a resistive divider is used to create the 1.8 V necessary for the hysteresis comparator to compare the reference voltage to. This is to enable the operation of the design under varying supply voltages, as the output voltage where the third stage starts operating will not be 9 V anymore. As mentioned, the resulting subtraction voltage with the offset is also the reference voltage for the charge pump, enabling it to track the electrode voltage. This part of the adaptive voltage supply enables its use with any constant current neural stimulation device as it tracks the electrode voltage in real time. In cases where more than three stages of charge are utilized, flash ADC must be modified, and bit mapping must be modified accordingly.

The adaptive voltage supply generator which decreases average supply voltage and thus, the low average power consumption are provided.

The adaptive voltage supply generator where necessary voltage compliance is roughly achieved by controlling the number of charge pump stages, where maximum number of charge pump stages is established by the voltage range of the stimulation circuit.

The adaptive voltage supply generator where the fine tuning of the necessary voltage compliance is performed by pulse frequency modulation (PFM) control, for which the reference is provided by the monitoring circuit with a certain amount of headroom to provide the scaled electrode voltage.

Thanks to the scaled electrode voltage, enabling real time tracking of the electrode voltage when used as a reference for the regulation system.

Figure 8:
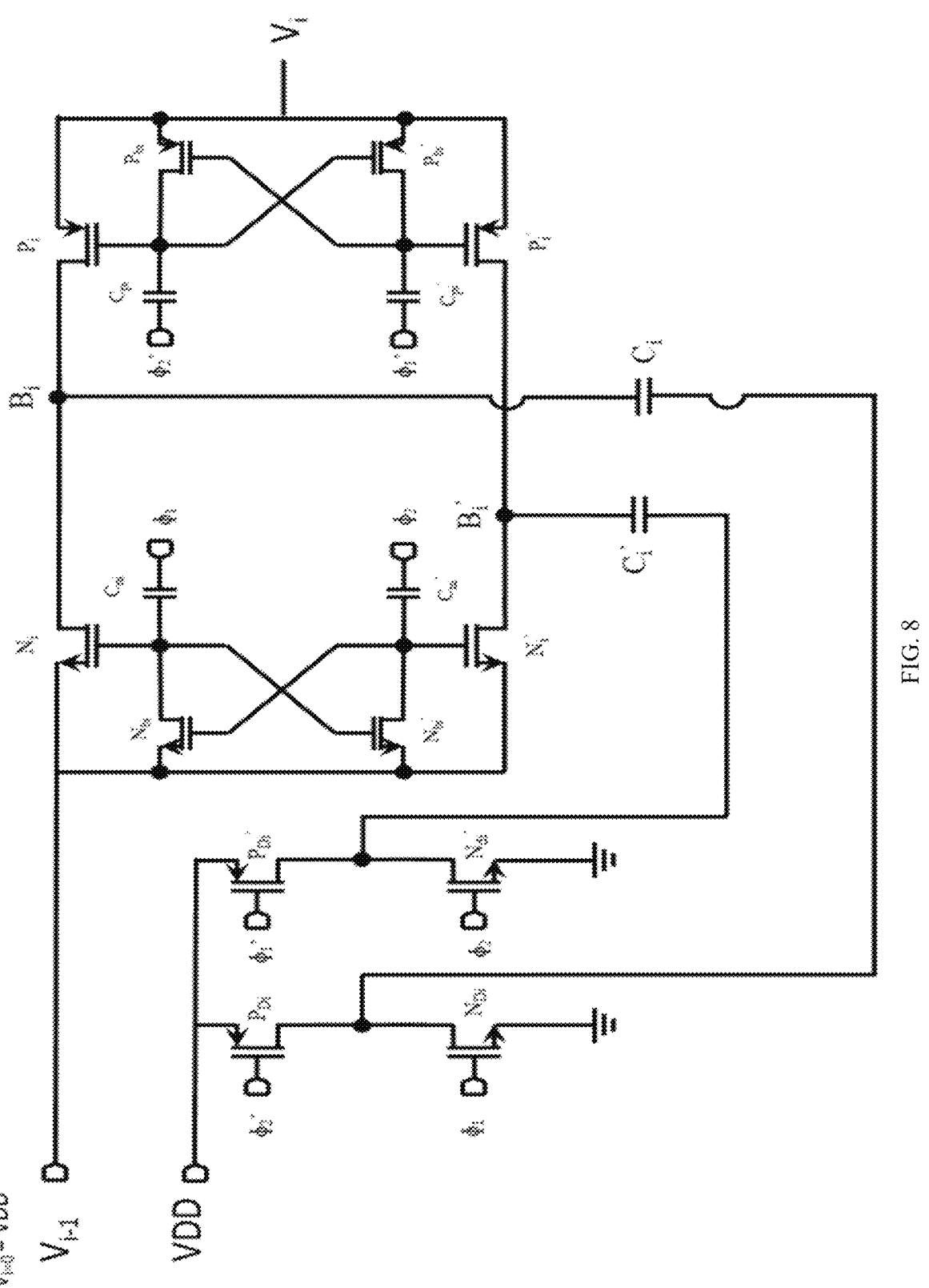
FIG. 8: One stage charge pump with bootstrapping capacitors.
Figure 9:
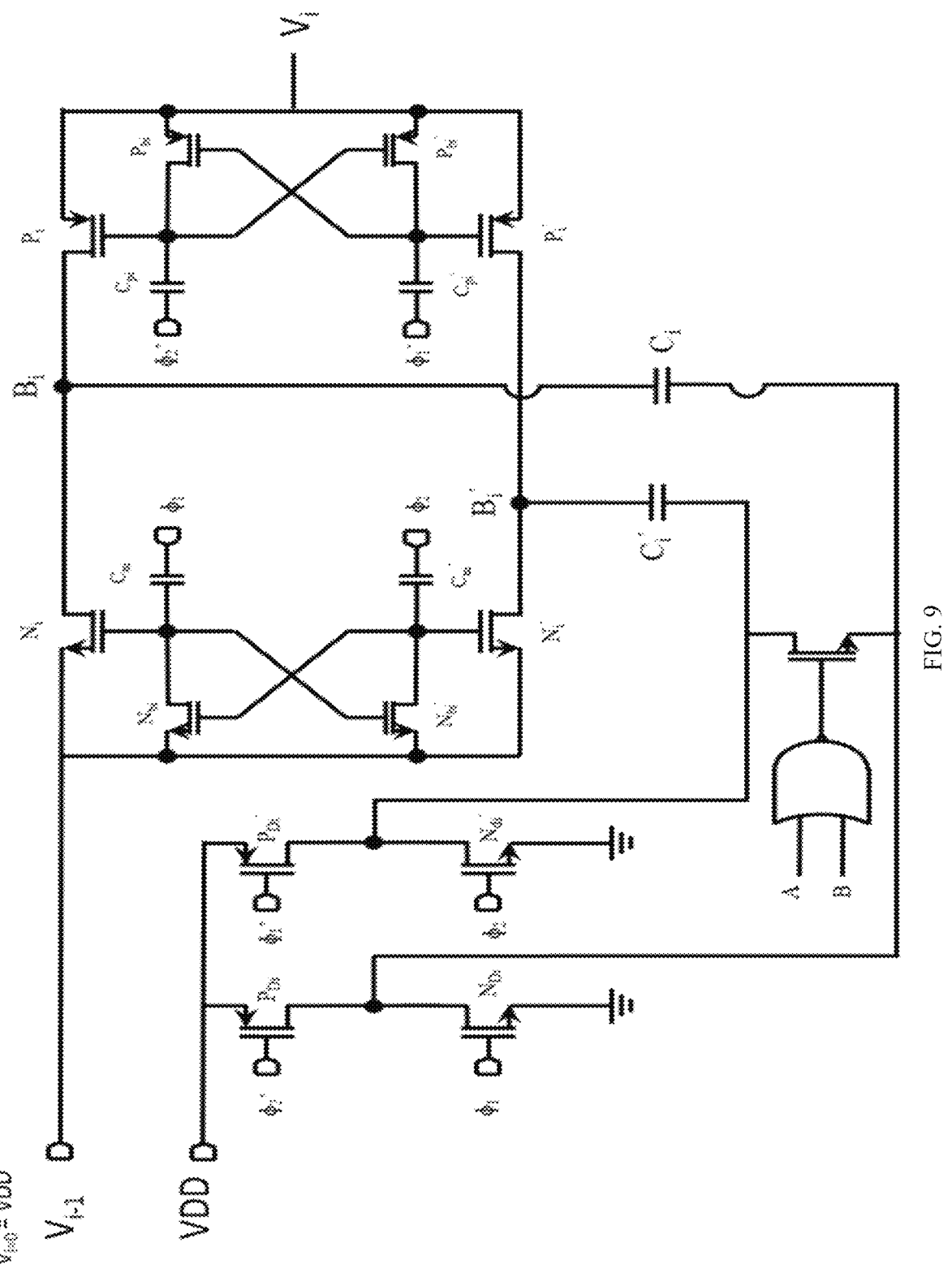
FIG. 9: One stage charge pump with charge reuse and bootstrapping capacitors.

Charge Pump:

One stage of the charge pump circuit is given in FIG. 8. It utilizes two charge transfer capacitors. Node B'$_i$ or B$_i$ are charged to $V_{i-1}$ in one phase and then boosted with the input voltage. In other words, when $\phi_i$ is HIGH, B$_i$ is equal to $V_{i-1}$ and when $\phi_2$ is HIGH, it is boosted with the input voltage. The same operation is valid for B'$_i$ as the charge pump is double configuration. In addition to the bootstrapping method, a charge reusing scheme is adopted to decrease the effects of bottom plate parasitics of on-chip MIM capacitors [10], this version is shown in FIG. 9: The charge pump in this design is a three-stage version of the circuit given below to be able to get 12 V at the output from a 3.3 V input.

Regulation:

As mentioned, two different methods are utilized to regulate the output of the charge pump. Rough regulation is performed by changing the number of charge pump stages operational. This is done with a flash ADC using three hysteresis comparators. The outputs of these comparators are mapped to two bits Bit_1 and Bit_2, which as explained before, determine the number of operational stages. The comparing voltages for these comparators are created by dividing the input voltage with the same ratio the output voltage of the charge pump is divided by to perform fine regulation, which is explained next. As mentioned before, creating the comparing voltage in this way enables the adaptive voltage supply to operate at varying battery voltages, e.g. it utilizes two stages of the charge pump if the desired output voltage is between two times and three time the input voltage.

For fine regulation of the charge pump voltage, PFM control method is adopted. The operational trans-conductance amplifier used as error amplifier compares the divided output of the charge pump with a reference voltage. According to its output, the control voltage of the oscillator is adjusted so that the switching frequency can change according to the load current. This way, the output impedance of the charge pump is adjusted, and its output voltage is kept at a desired value. In other examples, ripple-based regulation can be used as well.

Non-Overlapping Clock and Drivers:

For the proper operation of the charge pump, non-overlapping phases are needed. This is necessary to eliminate the short circuit losses of the charge pump. When switching, if the transistors that should not be on at the same time are on due to timing delays, a short-circuit path will be formed, which will degrade the efficiency. Thus, to prevent this, a conventional non-overlapping generator is used, and the clock signals are fed to the switches with a chain of drivers.

Electrode Voltage Sampling:

In the block diagram shown previously, it was stated that the electrode voltage across its terminals were used to as a reference voltage for the error amplifier and for control for number of charge pump stages operational. Important parts are explained here.

Figure 10:
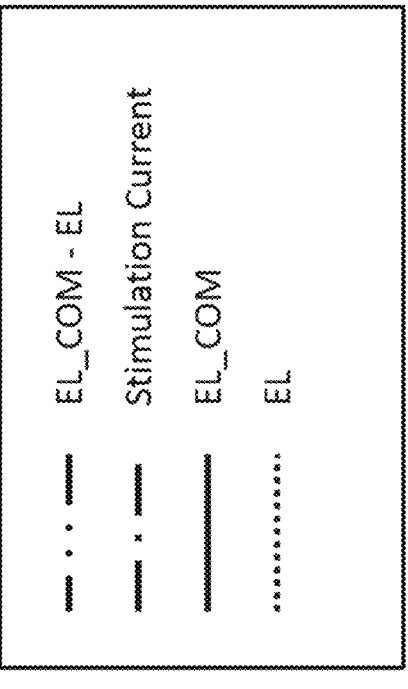
FIG. 10: Biphasic stimulation current, corresponding electrode voltage differences and individual electrode voltages.
Figure 10:
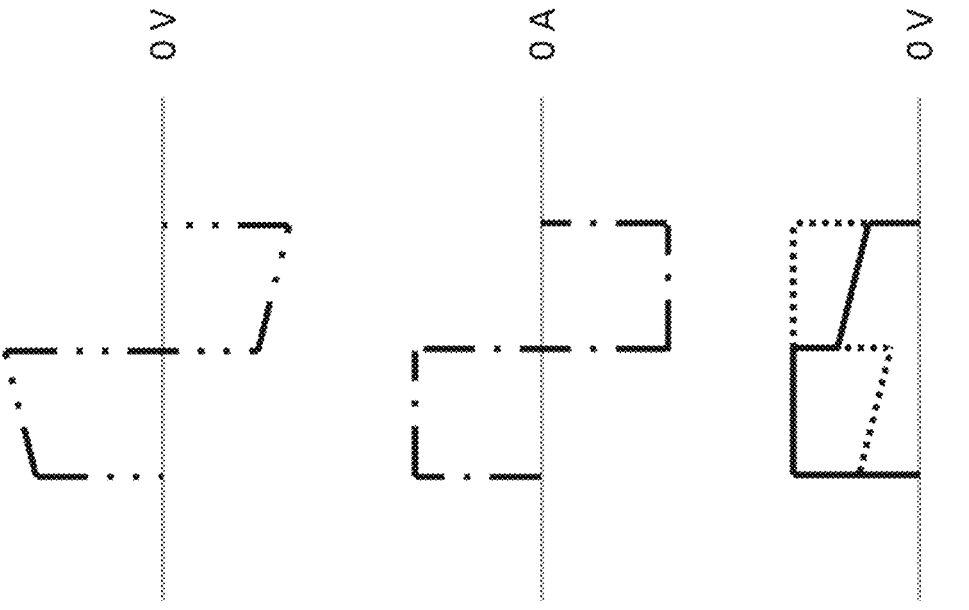
Figure 11:
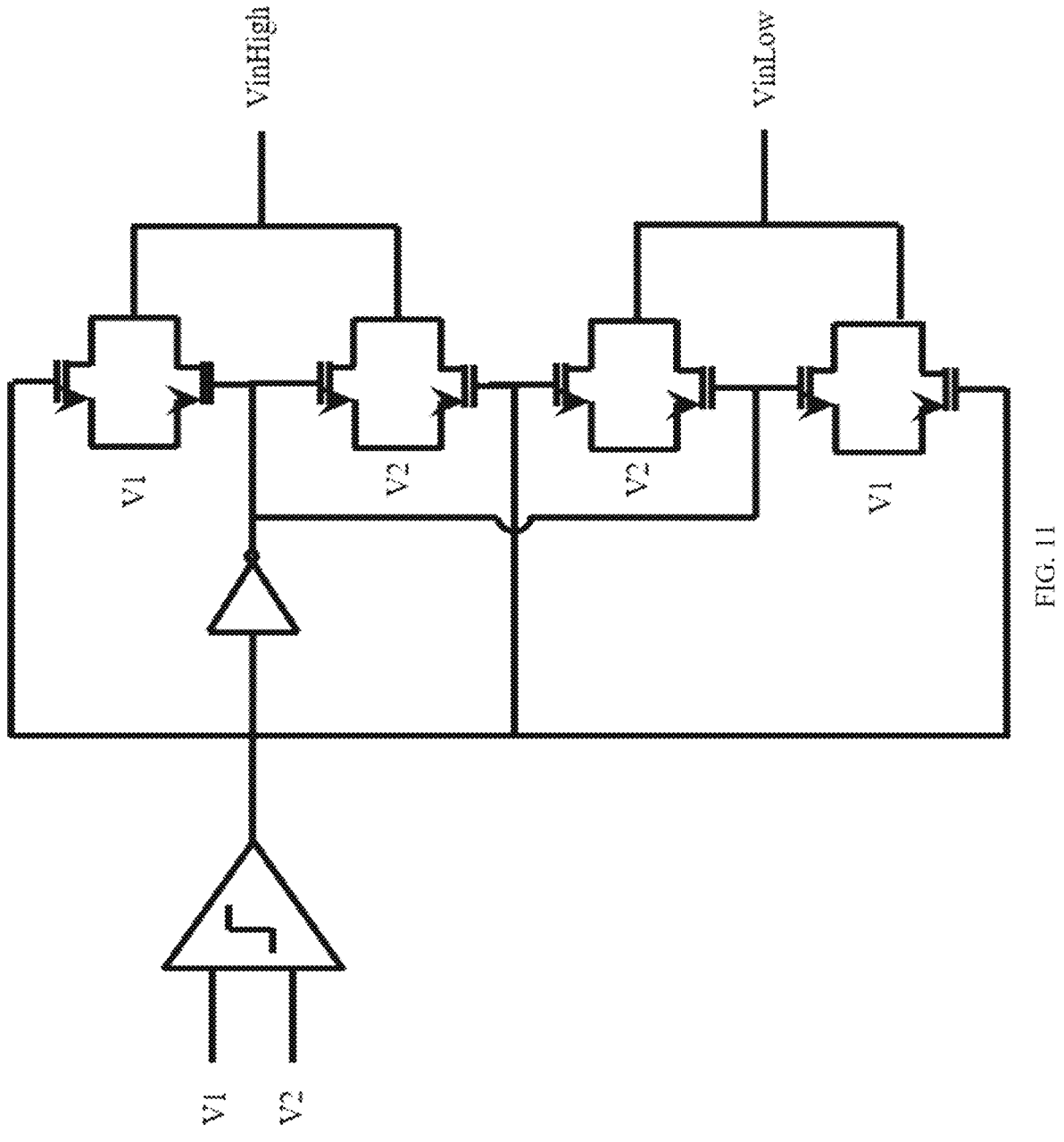
FIG. 11: Magnitude comparison circuit for electrode voltages.

Magnitude Comparison:

The biphasic stimulation and electrode voltage difference is reiterated in FIG. 10. In this figure the individual voltages of the electrodes is also shown. In one phase of the stimulation, one electrode voltage is greater and the vice versa for the other phase. Thus, to perform correct subtraction, magnitude comparison must be performed to determine which voltage is subtracted from which voltage. The circuit used for this purpose is given in FIG. 11.

Figure 12:
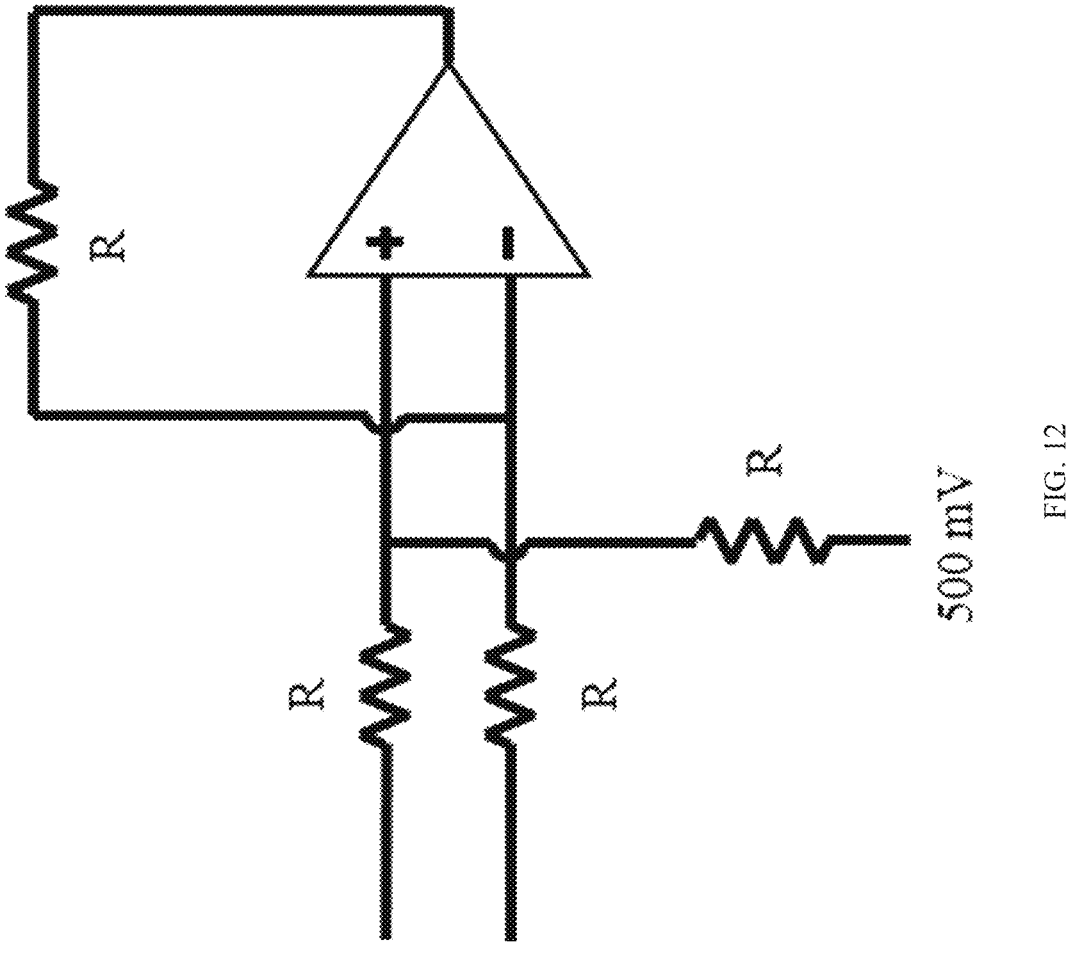
FIG. 12: Difference amplifier used for electrode voltage subtraction.

Subtraction:

For subtraction, a difference amplifier, as shown in FIG. 12 is implemented. For the amplifier, a folded cascode structure is used. An offset is given to the difference of electrodes to provide headroom between the switch matrix and the charge pump output voltage.

Figure 13:
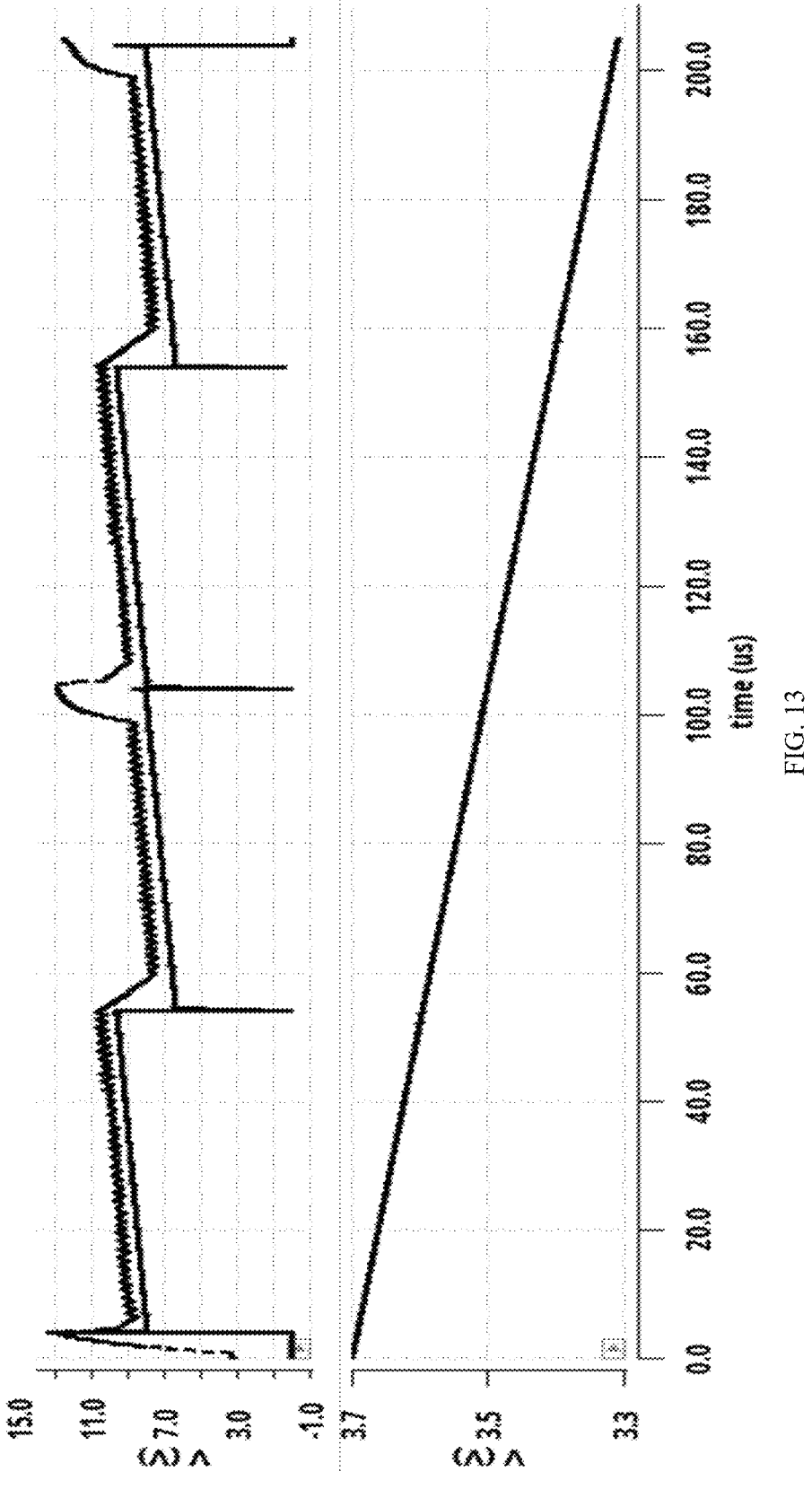
FIG. 13: Example waveform for charge pump output and absolute value of electrode voltages for identical load when battery voltage (bottom) is varied from 3.7 V to 3.3 V in 200 μs.

Simulations:

Simulations results for a few scenarios for the charge pump output voltage following the electrode voltage are provided in this section. FIG. 13 shows two consecutive stimulation periods in which the same load, as shown in Table 2, is used for the same stimulation current. The only thing that is changing is the supply voltage. As can be seen in the bottom waveform, the supply voltage is varied from 3.7 V to 3.3 V in a time interval of 200 µs. Despite this, the electrode voltage and the adaptive supply voltage remain the same and thus, it is shown that the system can work under varying supply voltages. FIG. 14 also shows two consecutive stimulation periods where the supply is decreased from 3.7 V to 3.3 V, however, this time the loads differ as well, and their values are provided in Table 3.

TABLE 2

| Stimulation conditions for waveforms in FIG. 13 | | |
| --- | --- | --- |
| Stimulation # | $R_{load}$ | $C_{load}$ |
| $1^{st}$ Electrode | 8 kΩ | 30 nF |
| $2^{nd}$ Electrode | 8 kΩ | 30 nF |

$I_{stimulation}$ = 1 mA

TABLE 3

| Stimulation conditions for waveforms in FIG. 14 | | |
| --- | --- | --- |
| Stimulation # | $R_{load}$ | $C_{load}$ |
| $1^{st}$ Electrode | 8 kΩ | 30 nF |
| $2^{nd}$ Electrode | 6.5 kΩ | 40 nF |

$I_{stimulation}$ = 1 mA

A monitoring circuit for measuring the electrode voltage compliance and controlling the voltage supply generator and monitoring circuit includes a voltage subtracting circuit with sign correction method to be applicable for any neural stimulation system and also includes digitalizing circuit to change the number of charge pump stages operational, A powering system, providing adaptive supply voltage for constant current neural stimulators including;

An adaptive voltage supply generator, configured to be connected to an energy source to output desired voltage levels and to decrease average supply voltage, and said adaptive voltage supply generator is configured to generate the necessary voltage compliance with energy sources having varying voltage levels and provide it to the switch matrix, which is used to create the necessary stimulation signal for the stimulation electrodes, A monitoring circuit, for measuring the electrode voltage compliance and control the voltage supply generator and said monitoring circuit includes a voltage subtracting circuit that continuously provides the electrodes' voltage difference to the supply generator so that it can track this voltage and enable it to adapt itself to any changes that occur during stimulation, a digitalizing circuit to change the number of charge pump stages operational, A charge pump, tracking the electrode voltage by control of number of charge pump stages utilized and control of frequency, A step-down converter, configured to be connected to energy source to power the monitoring circuit and power the control circuitry to bring down the power loss and said step-down converter is used to decrease the power dissipation of the control circuitry, A battery which is charged by using an energy harvester with the utilization of the interface circuitry or external source.

A battery can be rechargeable battery.

Another aspects of the invention;

The system further including an energy harvester system that is configured to charge the rechargeable battery and said energy harvester system includes interface circuit to recharge battery and scavenge ambient energy, Adaptive voltage supply generator that is structured to be controlled by the number of charge pump stages for necessary voltage compliance Adaptive voltage supply generator that uses pulse frequency modulation (PFM) control for fine tuning of the necessary voltage compliance.

The charge pump circuit includes level shifters to handle switches that connect the charge pump stages to the output, Adaptive voltage supply generator utilizes a three-stage charge pump, Adaptive voltage supply and the step-down converter use a battery as an energy source for operating, Step-down converter includes of a switched-capacitor converter,

9

Step-down converter is resonant converter, multi-level switching converter or linear converter, External source is a wireless power transmitter.

Scavenge ambient energy with piezoelectric or a similar energy generator system to contribute to the battery level by obtaining energy from the environment where the device is located.

The operation method of the system, the method including;

Generating the control signals via the control circuitry to start the charge pump and pull its output to maximum.

Generating the control signals via the control circuitry for the switch matrix to start the simulation period, Enabling of the voltage sampling circuitry and creation of scaled electrode voltage with an offset, Using the scaled electrode voltage as reference voltage for pulse frequency modulation control and to create signals for stage number control, Allowing the charge pump output to drop from its maximum to the value determined by the scaled electrode voltage and track it, Pulling the charge pump output via the control circuitry to its maximum with signals from the control circuitry before stimulation period ends to provide sufficient voltage for subsequent stimulation period, Keeping charge pump output at maximum until start signal for next stimulation period is given.

REFERENCES

[1] L. Yao, "Stimulator and Method for Processing a Stimulation Signal", United States Patent 20130314129A1, Nov. 28, 2013.

[2] L. P. Palmer, "Dual-Range Compliance Voltage Supply for a Multi-Channel Stimulator", U.S. Pat. No. 7,519,428B1, Apr. 14, 2009.

[3] D. J. Ternes, S. Vanderlinde, R. Vijayagopal, S. C. Boon, "Power Supply Management for Implantable Neurostimulation Devices", U.S. Pat. No. 9,079, 032B2, Jul. 14, 2015.

[4] J. Chen, "Charge Pump System, Devices and Methods for an Implantable Stimulator", U.S. Pat. No. 9,731, 116B2, Aug. 15, 2017.

[5] H. Ulusan, A. Muhtaroglu and H. Kulah, "A Sub-500 μW Interface Electronics for Bionic Ears", IEEE Access, vol. 7, pp. 132140-132152, 2019. Available: 10.1109/access.2019.2940744.

[6] W. Ngamkham, M. van Dongen and W. Serdijn, "Biphasic stimulator circuit for a wide range of electrode-tissue impedance dedicated to cochlear implants", 2012 IEEE International Symposium on Circuits and Systems, 2012. Available: 10.1109/iscas.2012.6271417.

[7] B. Swanson, P. Seligman, and P. Carter, "Impedance measurement of the Nucleus 22-electrode array in patients," Ann. Otol. Rhinol. Laryngol, vol. 104, no. 166, pp. 141-144, 1995.

[8] J. Sit and R. Sarpeshkar, "A Low-Power Blocking-Capacitor-Free Charge-Balanced Electrode-Stimulator Chip With Less Than 6 nA DC Error for 1-mA Full-Scale Stimulation", IEEE Transactions on Biomedical Circuits and Systems, vol. 1, no. 3, pp. 172-183, 2007. Available: 10.1109/tbcas.2007.911631.

[9] M. Makowski and D. Maksimovic, "Performance limits of switched-capacitor DC-DC converters", Proceedings of PESC '95-Power Electronics Specialist Conference. Available: 10.1109/pesc.1995.474969.

[10] Y. Allasasmeh and S. Gregori, "High-Performance Switched-Capacitor Boost-Buck Integrated Power Converters", IEEE Transactions on Circuits and Systems I: Regular Papers, vol. 65, no. 11, pp. 3970-3983, 2018. Available: 10.1109/tcsi.2018.2863239.

10

The invention claimed is:

1. A powering system, providing an adaptive supply voltage for constant current neural stimulators comprising;
   an adaptive voltage supply generator, configured to be connected to an energy source to output desired voltage levels and to decrease an average supply voltage, and wherein the adaptive voltage supply generator is configured to generate a necessary voltage compliance with energy sources having varying voltage levels and provide the necessary voltage compliance to a switch matrix, the switch matrix is configured to create a necessary stimulation signal for a stimulation electrode;
   a monitoring circuit, for measuring an electrode voltage compliance and control the voltage supply generator and the monitoring circuit comprises:
   a voltage subtracting circuit, wherein the voltage subtracting circuit continuously provides an electrode's voltage difference to the voltage supply generator and enable the voltage supply generator to adapt the voltage supply generator to any changes, wherein the any changes occur during a stimulation by tracking an electrode voltage,
   a digitalizing circuit to change a number of charge pump stages operational
   a charge pump, tracking the electrode voltage by a control of the number of the charge pump stages utilized and a control of a frequency;
   a step-down converter, configured to be connected to the energy source to power the monitoring circuit and power a control circuitry to bring down a power loss and wherein the step-down converter is configured to decrease a power dissipation of the control circuitry; and
   a rechargeable battery.

2. The powering system according to claim 1, further comprising an energy harvester system, wherein the energy harvester system is configured to charge the rechargeable battery.

3. The powering system according to claim 1, wherein the adaptive voltage supply generator is structured to be controlled by the number of the charge pump stages for the necessary voltage compliance.

4. The powering system according to claim 1, wherein the adaptive voltage supply generator is structured for a fine tuning of the necessary voltage compliance by pulse frequency modulation (PFM) control.

5. The powering system according to claim 1, wherein a charge pump circuit comprises a level shifter to handle switches, wherein the switches connect the charge pump stages to an output.

6. The powering system according to claim 1, wherein the adaptive voltage supply generator utilizes a three-stage charge pump.

7. The powering system according to claim 1, wherein an adaptive voltage supply and the step-down converter use a battery as an energy source.

8. The powering system according to claim 1, wherein the step-down converter comprises a switched-capacitor converter.

9. The powering system according to claim 1, wherein the step-down converter is one of the group consisting of a resonant converter, a multi-level switching converter and a linear converter.

10. The powering system according to claim 1, wherein an external source is a wireless power transmitter.

11. An operation method of the powering system according to claim 1, comprising;

generating control signals via the control circuitry to start the charge pump and pull an output of the charge pump to a maximum;

generating the control signals via the control circuitry for the switch matrix to start a simulation period;

enabling of a voltage sampling circuitry and a creation of a scaled electrode voltage with an offset;

using the scaled electrode voltage as a reference voltage for a pulse frequency modulation control and to create signals for a stage number control;

allowing the charge pump output to drop from the maximum to a value determined by the scaled electrode voltage and track the charge pump output;

pulling the charge pump output via the control circuitry to the maximum with signals from the control circuitry before the stimulation period ends to provide a sufficient voltage for a subsequent stimulation period; and keeping the charge pump output at the maximum until a start signal for a next stimulation period is given.

* * * * *